United States Patent [19]

Takasu

[11] Patent Number: 5,244,458
[45] Date of Patent: Sep. 14, 1993

[54] COLLAGEN GATHERING APPARATUS

[76] Inventor: Katsuya Takasu, 124-1, Aza-kamigochu, Oaza-akabane, Ishiki-cho, Hazu-gun, Aichi-ken, Japan

[21] Appl. No.: 753,764

[22] Filed: Sep. 3, 1991

[30] Foreign Application Priority Data

May 28, 1991 [JP] Japan ............... 3-154107

[51] Int. Cl.⁵ .............................. A61B 17/20
[52] U.S. Cl. ........................ 604/22; 604/902
[58] Field of Search ............ 604/22, 402, 35; 128/DIG. 8, 24 AA; 210/406, 416.1

[56] References Cited

U.S. PATENT DOCUMENTS

| 3,661,144 | 5/1972 | Jensen et al. | 604/22 |
| 4,250,892 | 2/1982 | Dolhay et al. | 604/22 |
| 4,468,217 | 8/1984 | Kuzmick et al. | 604/902 |
| 4,753,634 | 6/1988 | Johnson | 604/35 |
| 4,815,462 | 3/1989 | Clark | 604/22 |
| 4,886,491 | 12/1989 | Parisi et al. | 604/22 |
| 4,932,935 | 6/1990 | Swartz | 604/22 |
| 5,123,903 | 6/1992 | Quaid et al. | 604/22 |

Primary Examiner—Stephen C. Pellegrino
Assistant Examiner—Michael Rafa
Attorney, Agent, or Firm—Armstrong, Westerman, Hattori McLeland & Naughton

[57] ABSTRACT

A collagen gathering apparatus including a fat tissue crusher having a cannula which is inserted in a fat tissue to crush the fat tissue by an ultrasonic oscillation, a sucker having a suction pipe and a vacuum pump for sucking the fat tissue crushed by the crusher, and a collector which is connected to the suction pipe of the sucker and which has a filter for separating the fat tissue into a collagen and a liquid component.

14 Claims, 3 Drawing Sheets

COLLAGEN GATHERING APPARATUS

BACKGROUND OF THE INVENTION

1. Field of the Invention

The present invention relates to an apparatus for gathering collagen, and more precisely, it relates to an apparatus for crushing and sucking a fat tissue and separating it into collagen and liquid component.

2. Description of Related Art

For instance, in order to remove depressions, such as senile wrinkles or scars in a cosmetic surgery, it is known to directly inject collagen into his or her skin, using an injector, so that the depressions can be flattened. The collagen is made of fibrous protein which is a main component of a combined tissue which makes up a bone or skin, etc.

In a conventional cosmetic surgery, collagen is usually extracted from a cowhide and refined. However, there is a possibility of an occurrence of an allergic reaction due to heterogeneousness of the collagen (protein) from the human body.

To eliminate the problem with the allergic reaction, the inventors of the present invention have focused on the recent cosmetic surgery in which the fat is extracted from the buttocks or the belly and have proposed in Japanese patent Application No. 2-118016 that the collagen is extracted from the extracted fat and injected into his or her own skin. The collagen which is extracted from his or her own fat tissue is free from the allergic reaction due to heterogeneous protein.

In a conventional method for extracting the fat from the human body, a hollow tubular cannula is inserted into a subcutaneous tissue and is moved in the subcutaneous tissue to scrape the fat which is then sucked outward by a suction pump or the like through a passage formed in the cannula.

However, in the known method, there are drawbacks as follows:

(a) it is necessary for an operator to carefully and troublesomely move the cannula in the subcutaneous tissue which is mechanically crushed or destroyed by the cannula to scrape the fat from the subcutaneous tissue;

(b) it is difficult to precisely scrape the fat at a predetermined portion of the subcutaneous tissue by the cannula which is manually moved by an operator, thus resulting in a decrease in scientific reliability;

(c) there is a large possibility that a soft tissue other than fat can be injured by the movement of the cannula upon scraping the fat; and, (d) it is particularly difficult to control the bleeding from an cannula insertion portion of the human body and the soft tissue, injured by the cannula.

The primary object of the present invention is to eliminate the drawbacks mentioned above by providing a collagen gathering apparatus in which the fat can be effectively extracted from the human body and the collagen can be simply and effectively separated from the fat thus extracted.

Another object of the present invention is to provide a collagen gathering apparatus in which the fat can be precisely and simply taken out from a predetermined portion of the subcutaneous tissue by an operator to prevent the soft tissue other than the fat from being injured and to extremely decrease the bleeding.

SUMMARY OF THE INVENTION

To achieve the object of the present invention as mentioned above, there is provided a collagen gathering apparatus comprising a fat tissue crusher having a cannula which is inserted in a fat tissue to crush the fat tissue by an ultransonic oscillation, a sucker having a suction pipe and a vacuum pump for sucking the fat tissue crushed by the crusher, and a collagen collector which is connected to the suction pipe of the sucker and which has a filter for separating the fat tissue into a collagen and a liquid component.

BRIEF DESCRIPTION OF THE DRAWINGS

The invention will be described below in detail with reference to the accompanying drawings, in which.

DESCRIPTION OF THE PREFERRED EMBODIMENTS

Figure 1:
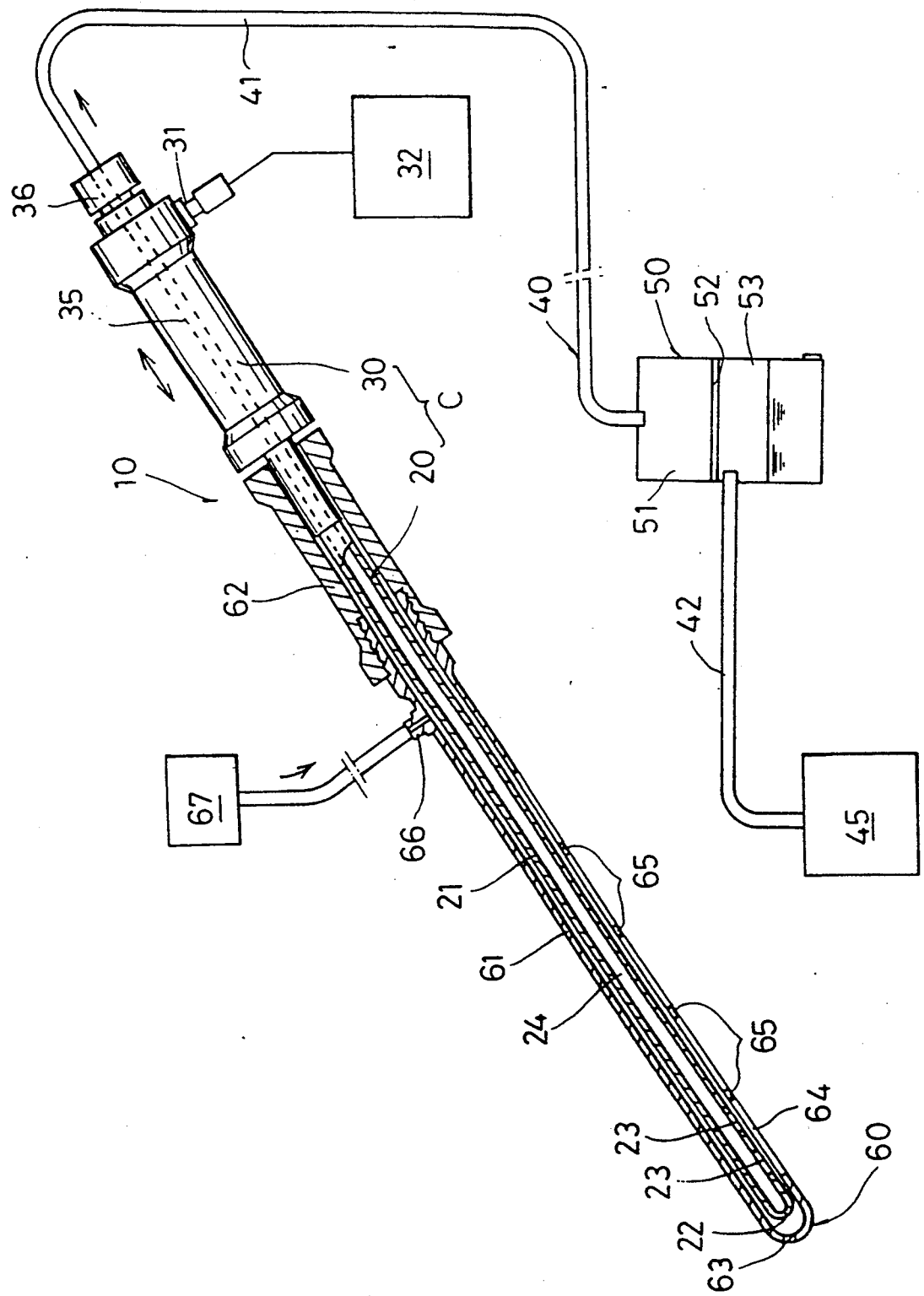
FIG. 1 is a partially sectioned side elevational view of a collagen gathering apparatus according to an aspect of the present invention.

As can be seen from FIG. 1, the collagen gathering apparatus of the present invention basically includes a fat tissue crusher 10, a sucker 40 and a collector 50.

Figure 2:
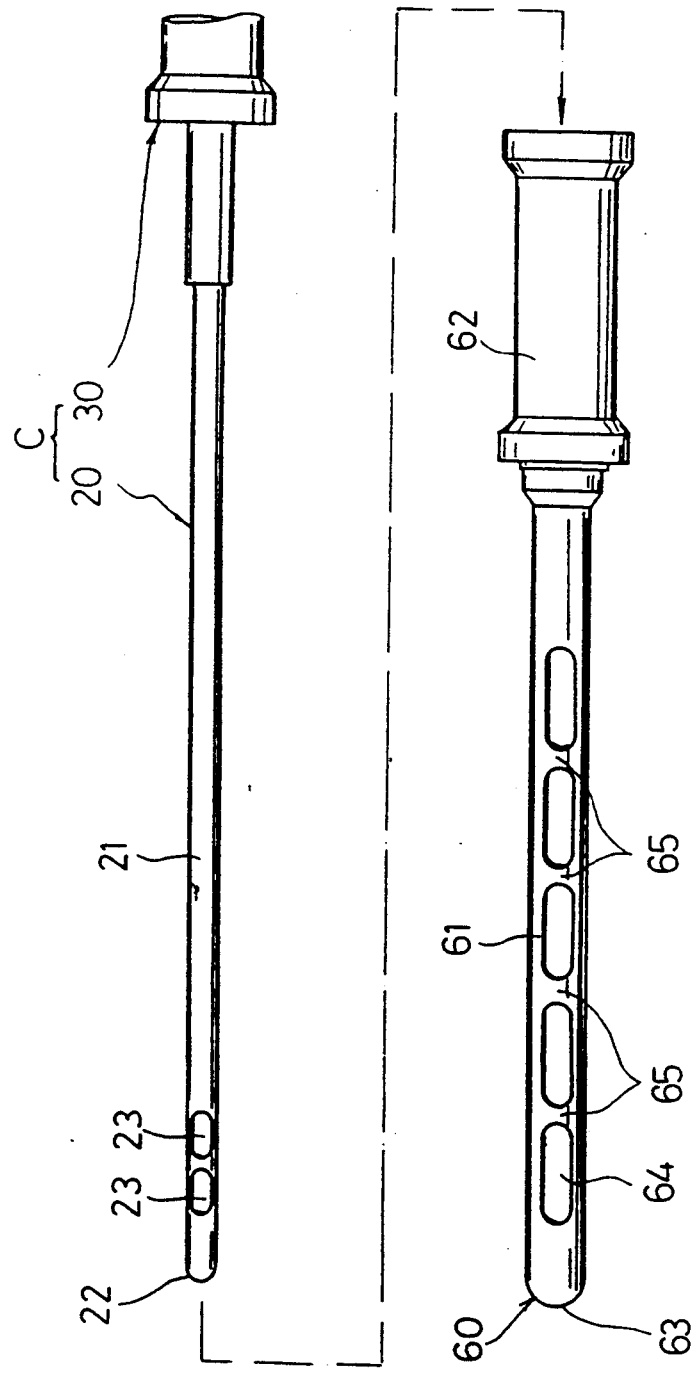
FIG. 2 is a schematic bottom view of a tip and an outer tube of a collagen gathering apparatus shown in FIG. 1.

The fat tissue crusher 10 has a cannula 20 which is comprised of a tip 20 and a hand piece 30 integral therewith. The tip 20 has a tubular body 21 of metal, such as titanium. The tip 20 is provided with a rounded front end 22 and sucking openings 23, 23 on the lower surface of the tube in the vicinity of the front end 22, as can be seen in FIG. 2. The tubular body 21 defines therein a suction passage 24 of the collagen which is crushed and extracted. In the illustrated embodiment, the tip 20 has 5 mm diameter and about 500 mm length.

The tip 20 is slidably inserted and supported in an outer tube 60. The outer tube 60 is made of light plastics having a high heat-resistance, such as fluoroplastics or the like. The outer tube 60 is comprised of a tubular body 61 which is inserted in the subcutaneous tissue and a grip portion 62 which is held by an operator.

The tubular body 61 protects the soft tissue from the movement of the tip 20 and heat due to the ultrasonic oscillation. The tubular body 61 also contributes to a precise removal of a predetermined fat tissue from the human body. The front end 63 of the tubular body 61 is rounded to prevent the skin and the subcutaneous tissue from being injured upon insertion of the tubular body. The tubular body 61 is provided on the lower surface thereof with an appropriate number of sucking openings 64 aligned along the length thereof, as shown in FIG. 2. Numeral 65 designates reinforcing bridge portions between the sucking openings 64. In the illustrated embodiment, the tubular body 61 has 10 mm diameter and about 340 mm length.

As can be seen in FIG. 1, the tubular body 61 is provided on its base end with a water supplying port 66 through which a coolant is fed from a coolant source 67 into the tubular body 61 to cool the heat produced in the tip 20, in accordance with need. The coolant is sucked together with the crushed fat. For example, a balanced saline solution or the like can be used as a coolant.

The tubular body 61 is screwed in and connected to the front end of the grip 62. The whole length of the outer tube 60 having the grip 62 and the tubular body 61 attached to the grip 62 is substantially equal to or slightly longer than the length of the tip 20.

The hand piece 30 is held by an operator to manually actuate the apparatus. The tip 20 is detachably connected to the front end of the hand piece 30. The hand piece 30 has an oscillation generating portion 31 and a suction passage 35.

The oscillation generating portion 31 is connected to a ultrasonic oscillator 32, so that the electric energy from the oscillator 32 is converted to the ultrasonic oscillation which is then transmitted to the tip 20 attached to the hand piece 30.

For instance, in the illustrated embodiment, the oscillation generating portion 31 generates the ultrasonic oscillation of 300 $\mu$m amplitude and 24000/sec frequency.

The ultrasonic oscillator 32 supplies the oscillation generating portion 31 of the hand piece 30 with electric energy which can be converted to the ultrasonic oscillation. In the illustrated embodiment, the ultrasonic oscillator 32 has an electrostrictive strain vibrator PZT of 24 kHZ of frequency of vibration and 100 W of maximum output.

The suction passage 35 is connected at its front end to the suction passage 24 of the tip 20 and at the rear end thereof to a front suction pipe 41 of the sucker 40, respectively. Numeral 36 designates a connecting portion of the suction pipe 41.

The sucker 40 has the front suction pipe 41 and a rear suction pipe 42, and a vacuum pump 45. The front suction pipe 41 is connected to the suction passage 35 of the hand piece 30, as mentioned above, so that the crushed fat tissue sucked from the sucking openings 23 of the tip 20 is forcedly sucked into the collector 50 by the vacuum pump 45 connected to the rear suction pipe 42.

Figure 3:
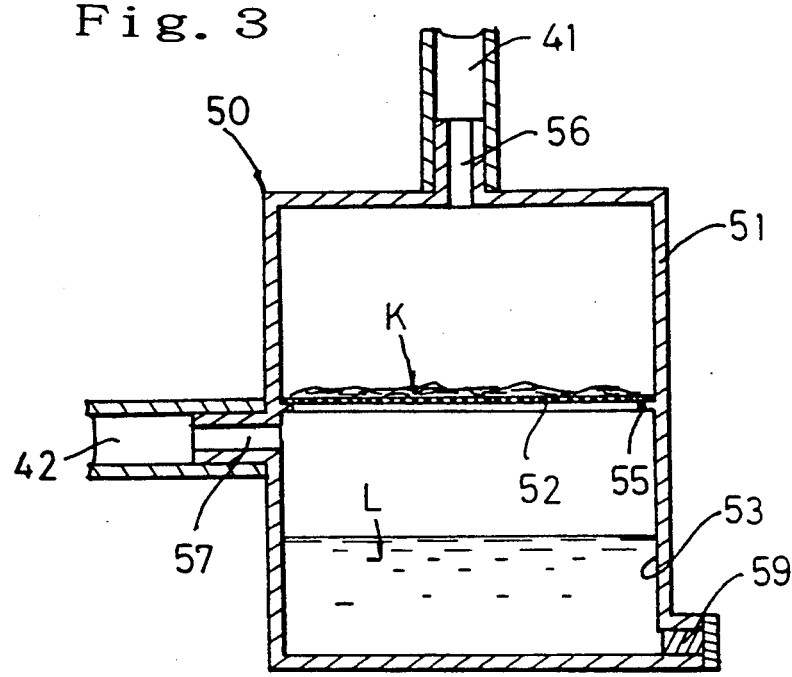
FIG. 3 is a sectional view of a collector according to a first embodiment of the present invention; and, FIG. 4 is a sectional view of a collector according to another embodiment of the present invention.

The collector 50 is located between the front and rear suction pipes 41 and 42 of the sucker 40, as shown in FIG. 3. The collector 50 has a body casing 51 and a filter 52 in the body casing 51. The crushed and sucked fat tissue is introduced in the body casing 51 and separated into the collagen K and the liquid component L by the filter 52. The filter 52 is held on and by a flange portion 55 of the body casing 51. The body casing 51 has an inlet port 56 connected to the front suction pipe 41 and an outlet port 57 connected to the vacuum pump 45 through the rear suction pipe 42.

The filter 52 has a filtering efficiency large enough to separate the collagen K of the fibrous component from the crushed fat tissue and can be realized, for example by a filtering film of polyester or nylon of about 100~500$\mu$ of opening diameter and 50~100$\mu$ of wire diameter, used in a known blood transfusion instrument.

The crushed fat tissue passing through the suction pipe 41 is rapidly separated into the liquid components L, such as water, oil, blood, lymph, etc., and the collagen K of fibrous component by the filter 52 of the collector 50. The liquid components L pass through the filter 52 and are collected in a reservoir 53 defined by the lower portion of the body casing 51. The collagen K is collected on the filter 52. Numeral 59 designates a liquid discharging port.

Figure 4:
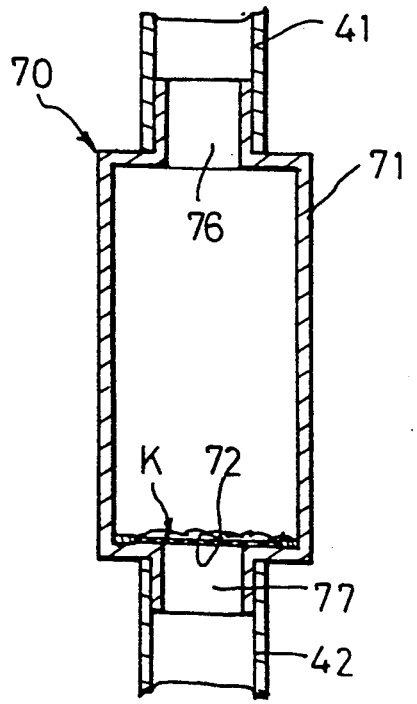

FIG. 4 shows a modified collector 70. In this embodiment, the crushed fat tissue passing through the suction pipe 41 is introduced into a tubular casing 71 through an inlet port 76, so that the collagen K is separated and collected from the fat tissue by the filter 72 provided at the outlet end (lower end) of the tubular casing 71. The liquid components past the filter 72 are collected in a reservoir (not shown) connected to the suction port 77 of the tubular casing 71.

The collagen thus obtained can be directly used as an autocollagen to himself or herself. It is possible to freeze the collagen for a long preservation, so that the frozen collagen can be defrosted to be used, in accordance with need.

As can be understood from the foregoing, according to the present invention, the fat tissue is directly crushed by the ultrasonic oscillation of the fat tissue crusher, and is sucked by the sucker, so that the collagen is separated from the fat tissue and collected in the collector.

According to the invention, since the fat tissue is directly crushed by the ultrasonic oscillation of the crusher, the crushed fat is extracted as it were melted butter. Consequently, the collagen can be simply and easily separated and collected from the crushed and extracted fat tissue only by the filter without using a special separating apparatus, such as a centrifugal separator.

Furthermore, according to the present invention, since no mechanical crush or destruction of the fat tissue takes place, unlike the prior art, the bleeding can be controlled to be minimized.

In addition, the labor of the operator can be largely decreased, and the fat tissue can be precisely picked at a desired portion of the subcutaneous tissue.

Furthermore, since the intensity and frequency of the ultrasonic wave of the ultrasonic oscillator can be simply and easily controlled, the necessary ultrasonic oscillation can be easily obtained.

We claim:

1. A collagen gathering apparatus, comprising:
   a fat tissue crusher including a cannula, an outer tube containing said cannula, and an ultrasonic oscillator means for oscillating said cannula, said outer tube having a plurality of suction openings and a suction passage therein in communication with said plurality of suction openings, wherein said cannula can be inserted in fat tissue to crush the fat tissue by ultrasonic oscillation caused by said oscillator means;
   a suction means having a suction pipe in communication with said suction passage and a vacuum pump in communication with said suction pipe, for providing suction to said suction pipe to enable it to extract the fat tissue crushed by the crusher; and
   a collagen collector which is connected between said suction pipe of said suction means and said vacuum pump, said collagen collector having a filter with means for separating the fat tissue extracted by said suction pipe into a collagen component and a liquid component.

2. A collagen gathering apparatus according to claim 1, wherein said cannula comprises a tip portion having a tubular body which defines therein a portion of said suction passage and which has at least one of said plurality of suction openings at the front end of said tubular body, and wherein said cannula further comprises a hand piece to which said tip portion is detachably connected and which has therein a further portion of said suction passage which is connected to said portion of said suction passage in said tip portion of said cannula.

3. A collagen gathering apparatus according to claim 2, wherein said ultrasonic oscillator means is connected to said hand piece, wherein said ultrasonic oscillator means further comprises an ultrasonic oscillation generating portion connected to said hand piece which transmits the ultrasonic oscillation to said tip portion of said cannula.

4. A collagen gathering apparatus according to claim 3, wherein said ultrasonic oscillator means further comprises an ultrasonic oscillation source connected to said ultrasonic oscillation generating portion.

5. A collagen gathering apparatus according to claim 2, wherein said tip portion of said cannula can be slidably inserted and held in said outer tube.

6. A collagen gathering apparatus according to claim 5, wherein said outer tube is spaced apart from said tip portion of said cannula.

7. A collagen gathering apparatus according to claim 4, wherein said suction pipe comprises a front suction pipe which is connected for communication with said suction passage of said tip portion and of said hand piece, and a rear suction pipe which is connected for communication with said front suction pipe and said vacuum pump.

8. A collagen gathering apparatus according to claim 7, wherein said collector is located between said front suction pipe and said rear suction pipe.

9. A collagen gathering apparatus according to claim 8, wherein said collector further comprises a reservoir, for receiving said liquid component, so that said liquid component separated from the fat tissue can be collected in said reservoir.

10. A collagen gathering apparatus according to claim 9, wherein said filter collects thereon the collagen separated from the fat tissue.

11. A collagen gathering apparatus according to claim 2, further comprising a cooler means connected to said cannula, for cooling said tip portion of said cannula.

12. A collagen gathering apparatus comprising:
an ultrasonic oscillation crushing means, which can be inserted in a fat tissue of a human body, for crushing the fat tissue with an ultrasonic oscillation, said ultrasonic oscillation crushing means including a cannula, having a tip portion an outer tube containing said cannula, and an ultrasonic oscillator means for oscillating said cannula, said outer tube having a plurality of suction openings and a suction passage therein in communication with said plurality of suction openings, wherein said cannula can be inserted in fat tissue to crush the fat tissue by ultrasonic oscillation caused by said oscillator means;
a suction means for extracting the fat tissue crushed by said ultrasonic oscillation crushing means;
a passage means for conveying the extracted fat tissue therethrough;
a collecting means for collecting the fat tissue conveyed through the passage means; and,
a separating means for separating a collagen from the collected fat tissue, wherein said tip portion of said cannula can be slidably inserted and held in said outer tube.

13. A collagen gathering apparatus according to claim 12, further comprising an ultrasonic oscillation generating means for generating the ultrasonic oscillation.

14. A collagen gathering apparatus according to claim 13, further comprising a cooling means for cooling the apparatus.

* * * * *